US006565893B1

(12) United States Patent
Jones et al.

(10) Patent No.: US 6,565,893 B1
(45) Date of Patent: May 20, 2003

(54) PROCESS FOR PREPARING A DISINFECTANT CONTAINING SUSPENDED METALS

(75) Inventors: F. Larry Jones, Fern Park, FL (US); John K. Jones, Fern Park, FL (US)

(73) Assignee: Worldwide Pure Water, Inc., Nassau (BS)

( * ) Notice: Subject to any disclaimer, the term of this patent is extended or adjusted under 35 U.S.C. 154(b) by 0 days.

(21) Appl. No.: 09/251,982

(22) Filed: Feb. 17, 1999

(51) Int. Cl.$^7$ .................. A01N 59/00; A01N 59/02; A01N 59/16; C02F 1/68
(52) U.S. Cl. .................. 424/616; 424/618; 424/630; 424/637; 424/638; 424/649; 424/703; 424/710; 504/151; 504/152; 210/749; 210/757; 210/758; 210/759; 210/764
(58) Field of Search .................. 424/618, 630, 424/637, 638, 703, 710, 649, 616; 210/749, 757–759, 764; 504/151, 152

(56) References Cited

U.S. PATENT DOCUMENTS

| 629,861 | A | 8/1899 | Konrad |
|---|---|---|---|
| 1,642,089 | A | 9/1927 | Schreier |
| 2,250,390 | A | 7/1941 | Minaeff et al. |
| 2,734,028 | A | 2/1956 | Domogalla |
| 2,902,400 | A | 9/1959 | Moudry et al. |
| 2,944,967 | A | 7/1960 | Dunklin et al. |
| 3,531,568 | A | 9/1970 | Pensack |
| 3,702,298 | A | 11/1972 | Zsoldos et al. |
| 4,311,598 | A | 1/1982 | Verachtert |
| 4,608,247 | A | 8/1986 | Heinig, Jr. |
| 4,614,595 | A | 9/1986 | Azzarella et al. |
| 4,810,496 | A | 3/1989 | Jensen |
| 4,915,955 | A | 4/1990 | Gomori |
| 5,071,569 | A | 12/1991 | Caulfield et al. |
| 5,078,902 | A | 1/1992 | Antelman |
| 5,089,275 | A | 2/1992 | Antelman |
| 5,306,432 | A | 4/1994 | Puetz |
| 5,352,369 | A | 10/1994 | Heinig, Jr. |
| 5,437,858 | A | 8/1995 | Hungerbach et al. |
| 5,540,885 | A | 7/1996 | Pahlmark et al. |
| 5,700,377 | A | 12/1997 | Cox |
| 5,772,896 | A | 6/1998 | Denkewicz, Jr. et al. |
| 5,783,092 | A | 7/1998 | Brown et al. |

*Primary Examiner*—John Pak
(74) *Attorney, Agent, or Firm*—Baker Botts L.L.P.

(57) ABSTRACT

A process for preparing a disinfectant for use in swimming pools and the like. The process provides a formulation containing copper sulfate pentahydrate that will remain suspended so long as the formulation is maintained at a temperature above 40° F. The process includes the step of mixing the copper sulfate pentahydrate with water, sulfuric acid and ammonium sulfate at a temperature of 187° F.±10° F., then rapidly cooling the mixture to a temperature of 57–65° F. Colloidal silver or gold added to the formulation before the step of rapidly cooling will also remain suspended. Hydrogen peroxide may be added to enhance the performance of the disinfectant.

12 Claims, No Drawings

PROCESS FOR PREPARING A DISINFECTANT CONTAINING SUSPENDED METALS

FIELD OF THE INVENTION

This invention relates generally to the field of water treatment. This invention relates particularly to methods of preparing disinfectants for the use as water treatment agents. This invention relates specifically to a process for placing ammonium sulfate, copper sulfate pentahydrate, and colloidal silver into an aqueous solution that can be used to disinfect a swimming pool or the like without the precipitation of the metals.

BACKGROUND OF THE INVENTION

It is well known that the water in swimming pools, hot tubs and the like must be treated regularly to control the number and type of microorganisms living in the water. Untreated water in such aquatic systems may become unpleasing and/or unsafe for contact with humans.

Among the biocides commonly used to control microorganisms such as bacteria and algae are chlorine, bromine, quaternary ammonium, hydrogen peroxide, ozone, and ultraviolet radiation. Each of these biocides has unique advantages and disadvantages, with chlorine being the most commonly used by far. However, chlorine has certain disadvantages that are becoming of increasing concern to many users, including environmental hazards, irritation to the skin and eyes, and the need to re-apply it frequently to maintain its effectiveness. Alternative materials and methods for disinfecting aquatic systems are continually being developed and improved.

It is known to use certain metals and metal compounds to control microorganisms in aquatic systems. Copper sulfate ($CuSO_4$), silver (Ag) and gold (Au) are known to be effective biocides. The difficulty of using these metals and metal compounds is in the method of bringing them in contact with the water and the microorganisms in the water. Ideally these materials are mixed throughout the volume of water to be treated to maximize the expose of the microorganisms to the surface of the biocide material. However, because these materials are heavier than water, they tend to precipitate out of the water and accumulate on the bottom of any stagnant or slow flowing portion of the water volume. This not only reduces the effectiveness of the material as a biocide, but it also creates an unsightly coating on the surfaces of the pool or tub, and interferes with desirable life forms when used in a natural body of water. U.S. Pat. No. 4,608,247 issued to Heinig on Aug. 26, 1986 addresses this problem by placing the biocide material in a canister and passing the water to be treated through the canister so that it comes into contact with the biocide. Such mechanical systems are undesirable because they require additional piping and energy to move the water over the biocide. More importantly, by concentrating the biocide action into a small location, the remainder of the volume of water remains untreated, thereby permitting the microorganisms to multiply unimpeded until they are eventually passed over the biocide material. What is needed is a method for keeping metal and metal compound biocide materials in suspension in a swimming pool or the like.

Accordingly, it is an object of this invention to provide a process for preparing a disinfectant that includes a metal or metal compound that will not precipitate out when used in a swimming pool or the like.

SUMMARY OF THE INVENTION

This and other objects of the invention are achieved by a process for preparing an aqueous disinfectant having the steps of: providing a volume of distilled water; mixing sulfuric acid with the water; mixing ammonium sulfate with the water and sulfuric acid to form a base mixture; heating the base mixture to a temperature of 187° F.±10° F.; mixing copper sulfate pentahydrate with the heated base mixture to form a CSX mixture; cooling the CSX mixture rapidly to a temperature of 57–65° F.

DESCRIPTION OF THE INVENTION

The inventors have developed a process for combining various biocide materials into water in a manner that results in a formulation that can be stored and used without the precipitation of the metals and metal compounds included in the formula. The formulations provided as examples herein are described in volumes that can be handled conveniently by a single person using mixing equipment that is commonly available. The inventive process described herein can be practiced with larger and smaller quantities of materials in the same ratios as the examples provided.

A base formulation is prepared by first mixing distilled water with sulfuric acid. The mixing is preferably done in a stainless steel or stainless lined vat having a mixer attached thereto. The vat should be stainless because of the corrosive properties of the sulfuric acid, and an automatic mixer is preferred because of the importance of thorough mixing and the relatively long time periods for mixing described below. A system that pumps air into the bottom of a vat to cause agitation of the fluid in the vat may be used in lieu of a mechanical mixer. By example, eight gallons of distilled water are placed into a vat with a mixer running slowly. One gallon of 66 bomay sulfuric acid (93% concentration solution) is added to the water as it is being agitated. The water and sulfuric acid are then thoroughly mixed, for example by running the mixer for at least five minutes. Food grade sulfuric acid should be used for swimming pool applications or other applications where possible ingestion of the formulation by humans is possible. After the sulfuric acid and water are thoroughly mixed, nine ounces of ammonium sulfate powder is added to the mixture while the agitation of the mixture is continued to create the base formulation. Here again, the ammonium sulfate may be food grade for appropriate applications. The base formulation should be agitated for a period of time sufficient to dissolve the powdered ammonium sulfate and to blend the mixture fully, for example for at least fifteen minutes.

The base formulation is then combined with copper sulfate to form a CSX formulation that is useful as a disinfectant for swimming pools and the like. Continuing with the example above, the nine gallons of base formulation is then heated to a temperature of 187° F.±10° F. The heating of the formulation may be conveniently accomplished if the vat used to mix the formulation is a double-walled, jacketed design. By passing heated water through the jacket of the vat, the formulation fluid inside the vat is heated by conduction. Once the base formulation is heated to the desired temperature, the fluid is again agitated while eighteen pounds of granular copper sulfate pentahydrate ($CuSO_4 \cdot 5H_2O$) is added to create the CSX formulation. Here, again, food grade copper sulfate pentahydrate is preferred for swimming pool applications and the like. Agitation of the CSX formulation should continue at the elevated temperature for at least thirty minutes to ensure adequate mixing. The CSX formulation is then rapidly cooled to a temperature of 57–65° F. The cooling should be accomplished within a fifteen minute time period. Such rapid cooling may conveniently be accomplished by passing chilled water or other cooling fluid through the jacket of the vat. The specific gravity of the CSX formulation is about 1.181. The copper sulfate pentahydrate of the CSX formulation prepared in accordance with this process will remain dispersed and suspended unless the temperature of the formulation is reduced to about 40° F. Thus, the CSX formulation may be bottled, shipped, stored and used as a disinfectant for swimming pools and the like more conveniently and effectively than formulations containing copper sulfate pentahydrate prepared by prior art methods. In order to facilitate the rapid and even cooling of the formulation, and to avoid the local precipitation of copper sulfate pentahydrate near the walls of the vat if the cooling fluid is at a temperature of less than 40° F., it is desirable to continue the agitation of the formulation during the cooling step.

The CSX formulation may further be combined with colloidal silver to form a CCX-Y formulation, also useful as a disinfectant for an aqueous environment. Continuing with the example above, one gallon of 10 ppm colloidal silver aqueous solution may be added to the CSX formulation at an elevated temperature of 187° F.±10° F. The CSX formulation may be re-heated from ambient conditions if it had previously been cooled, or the silver may be added to the formulation prior to the step of cooling described above. In either case, the silver should be thoroughly mixed, for example by agitating the formulation for at least thirty minutes at the elevated temperature. The CCX-Y formulation is then rapidly cooled to a temperature of 57–65° F. The cooling should be accomplished within a fifteen minute time period, as described above for the CSX formulation. As with the CSX formulation, the metal and metal compounds in the CCX-Y formulation will remain in suspension as long as the formulation is maintained at a temperature above 40° F. Colloidal gold may be substituted for the colloidal silver in the inventive process with similarly effective results. The amount of silver or gold added may be determined by the desired disinfectant properties of the formulation.

The colloidal silver or gold aqueous solution may be prepared by an electrolysis process. An electrolyte is prepared by adding a salt to distilled water. The inventors have found that a small amount of seawater, for example eight drops, may be added to a gallon of distilled water to obtain the desired properties. Silver or gold material having a very high level of purity, for example 0.999% pure, is mechanically attached to a positive and/or negative electrode. The positive and negative electrodes are then immersed in the electrolyte and the electrolyte is heated to an elevated temperature less than the boiling point, for example 180–210° F. A low voltage is then applied across the electrodes. In one embodiment four 9-volt dry batteries are connected in series across the electrodes to drive the silver or gold into colloidal suspension in the aqueous solution. The current is applied for a time period long enough to bring the concentration of silver or gold in the electrolyte to a desired level, for example about one hour to achieve a concentration of 10 ppm silver or gold. The colloidal aqueous solution is then ready to be mixed with the CSX formulation.

Alternatively, the CSX formulation may be combined with hydrogen peroxide ($H_2O_2$) to form a CCX-Z formulation for use as a disinfectant. Continuing with the example described above for the CSX formulation, nine milliliters of 35% hydrogen peroxide, preferably food grade, may be added to the CSX formulation at the elevated temperature of 187° F.±10° F. The CSX formulation may be re-heated from ambient conditions, or the hydrogen peroxide may be added to the formulation prior to the step of cooling described above. In either case, the hydrogen peroxide should be thoroughly mixed, for example by agitating the formulation for at least thirty minutes at the elevated temperature. The CCX-Z formulation is then rapidly cooled to a temperature of 57–65° F. The cooling should be accomplished within a fifteen minute time period, as described above for the CSX formulation.

Each of the CSX, CCX-Y and CCX-Z formulations may be packaged for retail distribution, such as one, five or ten gallon bottles. Appropriate labeling should be applied to the bottles, not only for consumer safety and as instructions for proper use, but also including a warning that the product should be maintained at a temperature above 40° F. to avoid the precipitation of the biocide metals.

The above disclosure is given by way of example, not limitation. The full scope of the present invention is as set forth in the following claims.

What is claimed is:

1. A process for preparing an aqueous disinfectant comprising the steps of:

providing a volume of distilled water;

mixing sulfuric acid and ammonium sulfate with said distilled water to form a base formulation;

heating said base formulation to a temperature of 187° F.±10° F.;

mixing copper sulfate pentahydrate with said heated base formulation to form a CSX formulation; and cooling said CSX formulation rapidly to a temperature of 57–65° F. to form an aqueous disinfectant.

2. The process of claim 1, further comprising the step of maintaining the CSX formulation at a temperature above about 40° F. after the cooling step.

3. The process of claim 1, wherein the steps of providing distilled water, mixing sulfuric acid, mixing ammonium sulfate and mixing copper sulfate pentahydrate further comprise mixing said distilled water, sulfuric acid, ammonium sulfate and copper sulfate pentahydrate in a ratio equivalent to the ratio of 8 gallons of distilled water to 1 gallon of 93% concentration sulfuric acid to 9 ounces of ammonium sulfate powder to 18 pounds granular copper sulfate pentahydrate.

4. The process of claim 1 wherein the step of cooling the CSX formulation rapidly is provided by cooling within a 15 minute time period.

5. A process for preparing an aqueous disinfectant comprising the steps of:

providing a volume of distilled water;

mixing sulfuric acid and ammonium sulfate with said distilled water to form a base formulation;

heating said base formulation to a temperature of 187° F.±10° F.;

mixing copper sulfate pentahydrate with said heated base formulation to form a CSX formulation;

mixing an aqueous solution of colloidal silver or gold to the CSX formulation to form a CCX-Y formulation; and cooling said CCX-Y formulation rapidly to a temperature of 57–65° F. to form an aqueous disinfectant.

6. The process of claim 5 further comprising the step of maintaining the CCX-Y formulation at a temperature above about 40° F. after the cooling step.

7. The process of claim 5 further comprising the step of cooling and re-heating the CSX formulation before the step of mixing the aqueous solution of colloidal silver or gold to the CSX formulation to form the CCX-Y formulation.

8. The process of claim 5 wherein the step of cooling the CCX-Y formulation rapidly is provided by cooling within a 15 minute time period.

9. A process for preparing an aqueous disinfectant comprising the steps of:

providing a volume of distilled water;

mixing sulfuric acid and ammonium sulfate with said distilled water to form a base formulation;

heating said base formulation to a temperature of 187° F.±10° F.;

mixing copper sulfate pentahydrate with said heated base formulation to form a CSX formulation;

mixing an aqueous solution of hydrogen peroxide to the CSX formulation to form a CCX-Z formulation; and cooling said CCX-Z formulation rapidly to a temperature of 57–65° F. to form an aqueous disinfectant.

10. The process of claim 9 further comprising the step of maintaining the CCX-Z formulation at a temperature above about 40° F. after the cooling step.

11. The process of claim 9 further comprising the step of cooling and re-heating the CSX formulation before the step of mixing the aqueous solution of hydrogen peroxide to the CSX formulation to form the CCX-Z formulation.

12. The process of claim 9 wherein the step of cooling the CCX-Z formulation rapidly is provided by cooling within a 15 minute time period.

* * * * *